US012618790B2

(12) United States Patent
Yang et al.

(10) Patent No.: US 12,618,790 B2
(45) Date of Patent: May 5, 2026

(54) ENVIRONMENT DETECTION APPARATUS

(71) Applicant: TAIWAN SEMICONDUCTOR MANUFACTURING COMPANY LTD., Hsinchu (TW)

(72) Inventors: Ming Da Yang, Taichung (TW); Chun-Hsuan Lin, Hsinchu County (TW); Chwen Yu, Taipei (TW)

(73) Assignee: TAIWAN SEMICONDUCTOR MANUFACTURING COMPANY LTD., Hsinchu (TW)

( * ) Notice: Subject to any disclaimer, the term of this patent is extended or adjusted under 35 U.S.C. 154(b) by 358 days.

(21) Appl. No.: 18/495,719

(22) Filed: Oct. 26, 2023

(65) Prior Publication Data

US 2025/0137955 A1     May 1, 2025

(51) Int. Cl.
G01N 27/02 (2006.01)
G01N 33/00 (2006.01)

(52) U.S. Cl.
CPC ......... G01N 27/02 (2013.01); G01N 33/0027 (2013.01)

(58) Field of Classification Search
CPC ........................... G01N 27/02; G01N 33/0027
USPC ........................................................ 73/31.05
See application file for complete search history.

(56) References Cited

U.S. PATENT DOCUMENTS

| | | | |
|---|---|---|---|
| 2017/0057748 A1 | 3/2017 | Hoynash et al. | |
| 2019/0041371 A1* | 2/2019 | Dinsmore | G01N 27/4163 |
| 2021/0086194 A1* | 3/2021 | Ryu | F24F 8/192 |
| 2023/0313399 A1* | 10/2023 | Feng | C25B 15/085 |
| | | | 128/202.26 |

FOREIGN PATENT DOCUMENTS

| | | |
|---|---|---|
| CN | 108619878 A | 10/2018 |
| TW | 202022777 A | 6/2020 |
| WO | 2023186416 A1 | 10/2023 |

OTHER PUBLICATIONS

English Abstract Translation of CN108619878.
English Abstract Translation of TW202022777.
English Abstract Translation of WO2023186416.
Response Characteristics of a Stable Mixed Potential Ammonia Sensor in Simulated Diesel Exhaust Journal of The Electrochemical Society, 164 (9) B448-B455 (2017).

(Continued)

*Primary Examiner* — Peter J Macchiarolo
*Assistant Examiner* — John M Royston
(74) *Attorney, Agent, or Firm* — WPAT LAW; Anthony King

(57) ABSTRACT

An environment detection apparatus is provided. In one embodiment, the detection apparatus comprises: a first sensing device, a second sensing device in fluid communication with the first sensing device and a spectrum analyzer electrically connected to the first sensing device and the second sensing device. The first sensing device includes a pair of first electrodes configured to provide a first alternating current signal directly to a gas flowing into the first sensing device. The second sensing device includes a first filter configured to capture a solid in the gas flowing into the second sensing device and a pair of second electrodes configured to provide a second alternating current signal directly to the first filter with the solid captured by the first filter.

20 Claims, 11 Drawing Sheets

(56)     References Cited

OTHER PUBLICATIONS

Impedance Spectroscopy-Based Reduced Graphene Oxide-Incorporated ZnO Composite Sensor for H2S Investigations, ACS Omega 2019, 4, 9976-9982.
Gas Category and Concentration Detection Device. Rightek Co., Ltd. [retrieved on Oct. 26, 2023]. Retrieved from the Internet: <URL: https://www.rightek.com.tw/>.

* cited by examiner

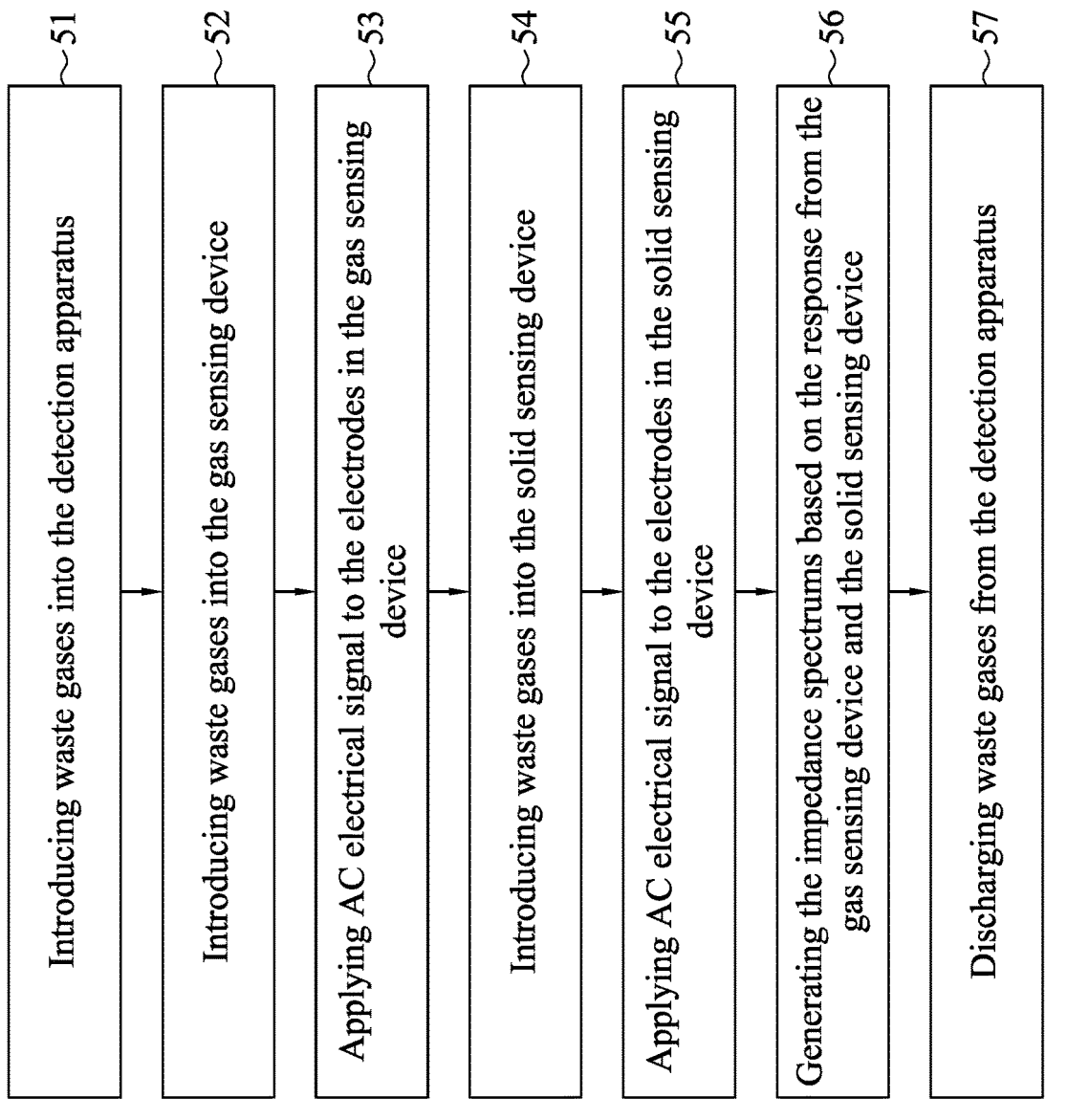

51 Introducing waste gases into the detection apparatus

52 Introducing waste gases into the gas sensing device

53 Applying AC electrical signal to the electrodes in the gas sensing device

54 Introducing waste gases into the solid sensing device

55 Applying AC electrical signal to the electrodes in the solid sensing device

56 Generating the impedance spectrums based on the response from the gas sensing device and the solid sensing device 57 Discharging waste gases from the detection apparatus

FIG. 5

ENVIRONMENT DETECTION APPARATUS

BACKGROUND

In the semiconductor industry, there is an increasing demand for stricter regulations on the emission of waste gases due to the requirement of achieving net zero emissions. Net zero emissions have become an important aspect of corporate social responsibility (CSR) for semiconductor companies. The semiconductor industry is known for its significant contribution to greenhouse gas emissions, particularly through the release of waste gases during the manufacturing process. These waste gases have a high global warming potential and can remain in the atmosphere for a long time, contributing to climate change.

To address this issue, governments and regulatory bodies are imposing more stringent regulations on waste gas emissions from semiconductor facilities. These regulations aim to reduce the industry's environmental impact and promote sustainable practices. Semiconductor companies are now required to invest in advanced emission control technologies and implement measures to minimize waste gas emissions. Achieving net zero emissions has become a crucial CSR goal for semiconductor companies. By committing to net zero emissions, these companies demonstrate their dedication to environmental sustainability and reducing their carbon footprint. This commitment involves not only complying with regulatory requirements but also actively seeking innovative solutions to minimize waste gas emissions throughout the entire manufacturing process. Furthermore, achieving net zero emissions can enhance the reputation and competitiveness of semiconductor companies. As sustainability becomes a key consideration for customers, investors, and other stakeholders, companies that prioritize environmental responsibility are more likely to attract business and investment opportunities. By aligning their CSR goals with net zero emissions, semiconductor companies can demonstrate their commitment to sustainable practices and differentiate themselves in the market.

Therefore, net zero emissions have become an important aspect of CSR for semiconductor companies, as they demonstrate a commitment to environmental sustainability and contribute to the overall sustainability of the industry. By investing in advanced emission control technologies and adopting cleaner manufacturing processes, semiconductor companies can reduce their environmental impact and enhance their reputation in the market.

However, there is currently no system or device available that can monitor and analyze the emissions of waste gases from semiconductor factories in real-time. Semiconductor manufacturers typically require complex and time-consuming analysis processes, such as the process of ion chromatography (IC) analysis, to determine if their emitted waste gases meet the requirements.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 5 is a flow chart representing a method for operating the detection apparatus in accordance with an embodiment of the present disclosure.

DETAILED DESCRIPTION

Figure 1:
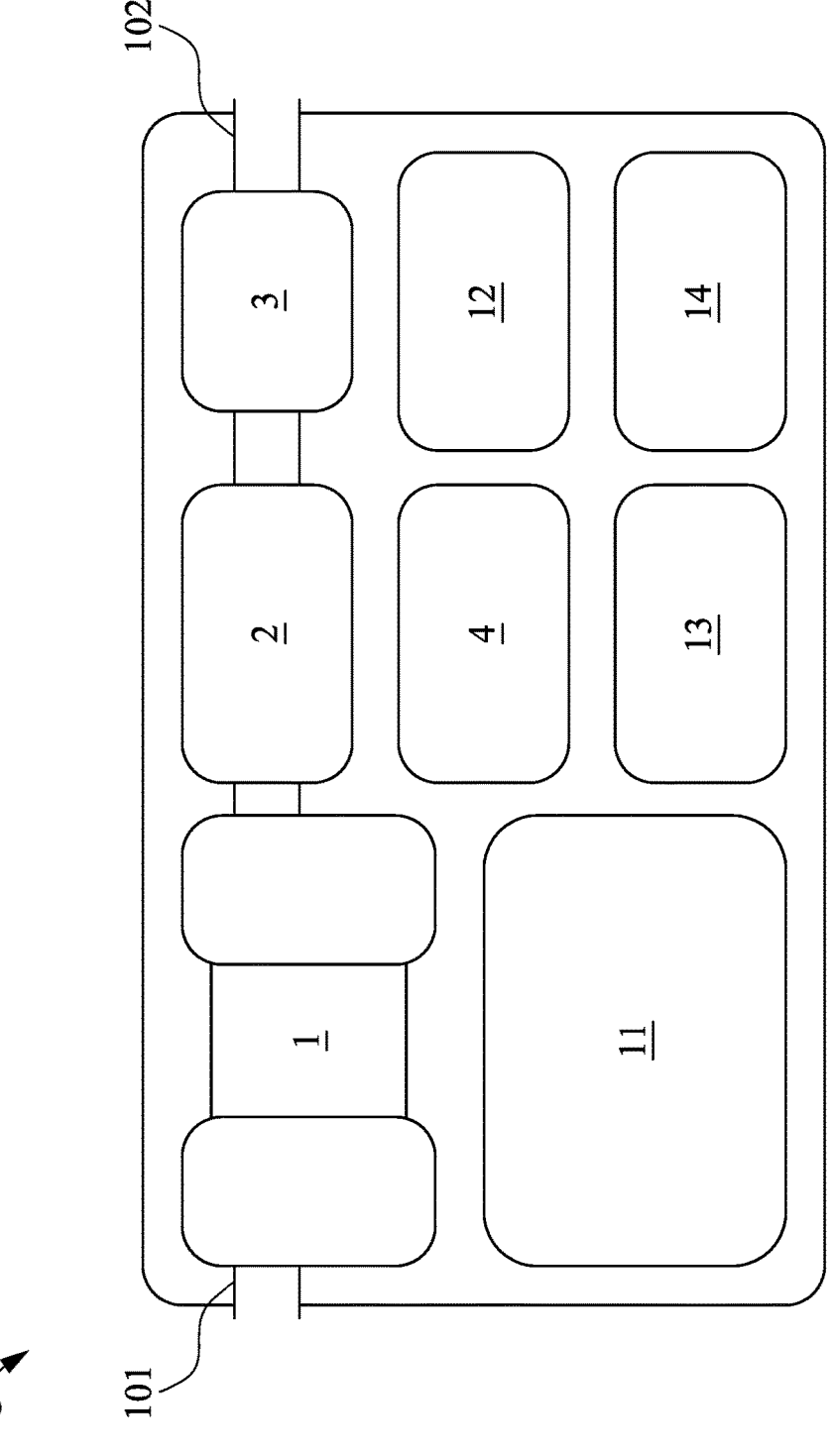
FIG. 1 is a schematic illustration of the detection apparatus in accordance with an embodiment of the instant disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

This description of illustrative embodiments is intended to be read in connection with the accompanying drawings, which are to be considered part of the entire written description. In the description of embodiments disclosed herein, any reference to direction or orientation is merely intended for convenience of description and is not intended in any way to limit the scope of the present disclosure. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected" and "interconnected," refer to a relationship wherein structures are secured or attached to one another either directly or indirectly through intervening structures, as well as both movable or rigid attachments or relationships, unless expressly described otherwise. Moreover, the features and benefits of the disclosure are illustrated by reference to the embodiments. Accordingly, the disclosure expressly should not be limited to such embodiments illustrating some possible non-limiting combination of features that may exist alone or in other combinations of features; the scope of the disclosure being defined by the claims appended hereto.

Present disclosure provides a detection apparatus for detecting and identifying characteristics of waste gases generated from semiconductor manufacturing. Examples of the present disclosure include detection apparatus and method thereof to detect an amount of impedance in gas. The impedances may be obtained through electrochemical impedance spectroscopy. Electrochemical impedance spectroscopy (e.g., EIS) is an electrochemical technique that may include application of a sinusoidal electrochemical pertubation (e.g., voltage or current) to a sample that covers a wide range of frequencies. Such a multi-frequency excitation may allow measurement of electrochemical reactions therein that take place at different rates and capacitance of a respective electrode.

FIG. 1 is a schematic view of a detection apparatus 10, in accordance with some embodiments of the present disclosure. In some embodiments of the present disclosure, the detection apparatus may include a power device 11, a gas sensing device 2, a solid sensing device 3, a spectrum analyzer 4, a power device 11, a display 12, a DAQ device 13 and a controller 14.

As shown in FIG. 1, the detection apparatus 10 may include an air inlet 101 and an air outlet 102. The waste gases generated from semiconductor manufacturing may be introduced into the detection apparatus 10 through the air inlet 101 and may be discharged from the detection apparatus 10 through the air outlet 102. Referring to FIG. 1, the pump 1 may be connected to the air inlet 101 and configured to introduce the waste gases from the outside of the detection apparatus 10 to the inside of the detection apparatus 10. In terms of usage, the detection apparatus 10 may be connected to the exhaust equipment of the semiconductor fabrication plant, such as chimneys, through a sampling hole to collect the waste gases. However, the interior of the exhaust equipment may be under negative pressure, and the waste gases cannot flow into the detection apparatus 10 on its own. Therefore, the pump 1 is needed to draw the waste gases from the sampling hole of the exhaust equipment into the detection apparatus 10.

Referring to FIG. 1, the pump 1 may be connected to the gas sensing device 2. The pump 1 may be in fluid communication with the gas sensing device 2. The gas sensing device 2 is configured to detect an impedance spectrum of the waste gases flowing into the gas sensing device 2. In some embodiments of the present disclosure, the gas sensing device 2 include at least two electrodes, which may apply different frequency AC (alternating current) electrical signals. The current and voltage responses between these electrodes may be transmitted to and recorded in the spectrum analyzer 4. The spectrum analyzer 4 may calculate complex impedance values based on these responses, and such measurements are performed at different frequencies, forming an impedance spectrum within a frequency range. That is, the impedance spectrum of the waste gases may be detected by the gas sensing device 2.

The solid sensing device 3 may be connected to the gas sensing device 2. The gas sensing device 2 may be in fluid communication with the solid sensing device 3. That is, the waste gases may flow from the gas sensing device 2 into the solid sensing device 3. The gas sensing device 2 is configured to detect an impedance spectrum of the solids in the waste gases flowing into the solid sensing device 3. In some embodiments of the present disclosure, the waste gases may include acid and alkaline gases. The acid and alkaline gases may include salt solids. That is, the solid sensing device 3 may be used to detect the impedance spectrum of such salt solids.

In some embodiments of the present disclosure, the solid sensing device may include at least two electrodes and a filter between the electrodes. When the waste gases flows into the solid sensing device 3, the solids in the waste gases may be collected by the filter and remained on the filter. The electrodes may apply different frequency AC (alternating current) electrical signals. The current and voltage responses between these electrodes may be transmitted to and recorded in the spectrum analyzer 4. The spectrum analyzer 4 may calculate complex impedance values based on these responses, and such measurements are performed at different frequencies, forming an impedance spectrum within a frequency range. That is, the impedance spectrum of the solids in waste gases may be detected by the solid sensing device 3.

The spectrum analyzer 4 may receive and record the current and voltage responses between the electrodes in the gas sensing device 2 and/or the current and voltage responses between the electrodes in the solid sensing device 3. The spectrum analyzer 4 may calculate complex impedance values based on these responses and result the impedance spectrum. That is, the spectrum analyzer 4 is configured to obtain the impedance spectrum detected by the gas sensing device 2 and the impedance spectrum detected by the sold sensing device. By analyzing the impedance spectrum resulted from the spectrum analyzer 4, users can infer or identify the characteristics of waste gases, such as their composition and concentration. In some embodiments of the present disclosure, the spectrum analyzer 4 may include a model that includes exhaust gas data and information. When the spectrum analyzer 4 generates the impedance spectrum, the generated impedance spectrum can be matched with the model to directly identify the characteristics of the waste gases. That is, the spectrum analyzer 4 may identify the characteristics of the waste gases based on the impedance spectrum detected by the gas sensing device 2 and/or the impedance spectrum detected by the solid sensing device 3.

The power device 11 may include a power supply. The power device 11 is configured to provide power to the pump 1, the gas sensing device 2, the solid sensing device 3, spectrum analyzer 4, the display 12, the DAQ device 13 and/or the controller 14.

The display 12 is configured to provide information to the users. In some embodiments of the present disclosure, the display 12 may provide a result of the impedance spectrum generated by the spectrum analyzer 4. For example, the display 12 may display an Electrochemical Impedance Spectroscop. In some embodiments of the present disclosure, the Electrochemical Impedance Spectroscop may include Nyquist plot and Bode plot. In some embodiments of the present disclosure, the display 12 may display the characteristics of the waste gases. For example, the display 12 may display the compositions and concentrations of the waste gases.

In some embodiments of the present disclosure, the DAQ device 13 is configured to receive and record the current and voltage response from the gas sensing device 2. In some embodiments of the present disclosure, the DAQ device 13 is configured to receive and record the current and voltage response from the solid sensing device 3. In some embodiments of the present disclosure, the DAQ device 13 is configured to receive and record the current and voltage response from the gas sensing device 2 and/or the current and voltage response from the solid sensing device 3 through the spectrum analyzer 4. In some embodiments of the present disclosure, the DAQ device 13 is configured to receive and record the impedance spectrums generated from the spectrum analyzer 4. The DAQ device 13 may include, but not limited to, Analog to Digital Converter (ADC), data logger, signal conditioning circuitry, multiplexer, and Time to Digital Converter (TDC).

The controller 14 may include a programmable logic controller (PLC). In some embodiments of the present disclosure, the controller 14 is configured to control the pump 1, the gas sensing device 2, the solid sensing device 3, the spectrum analyzer 4, the power device 11, the display 12 and/or the DAQ device 13.

Figure 2:
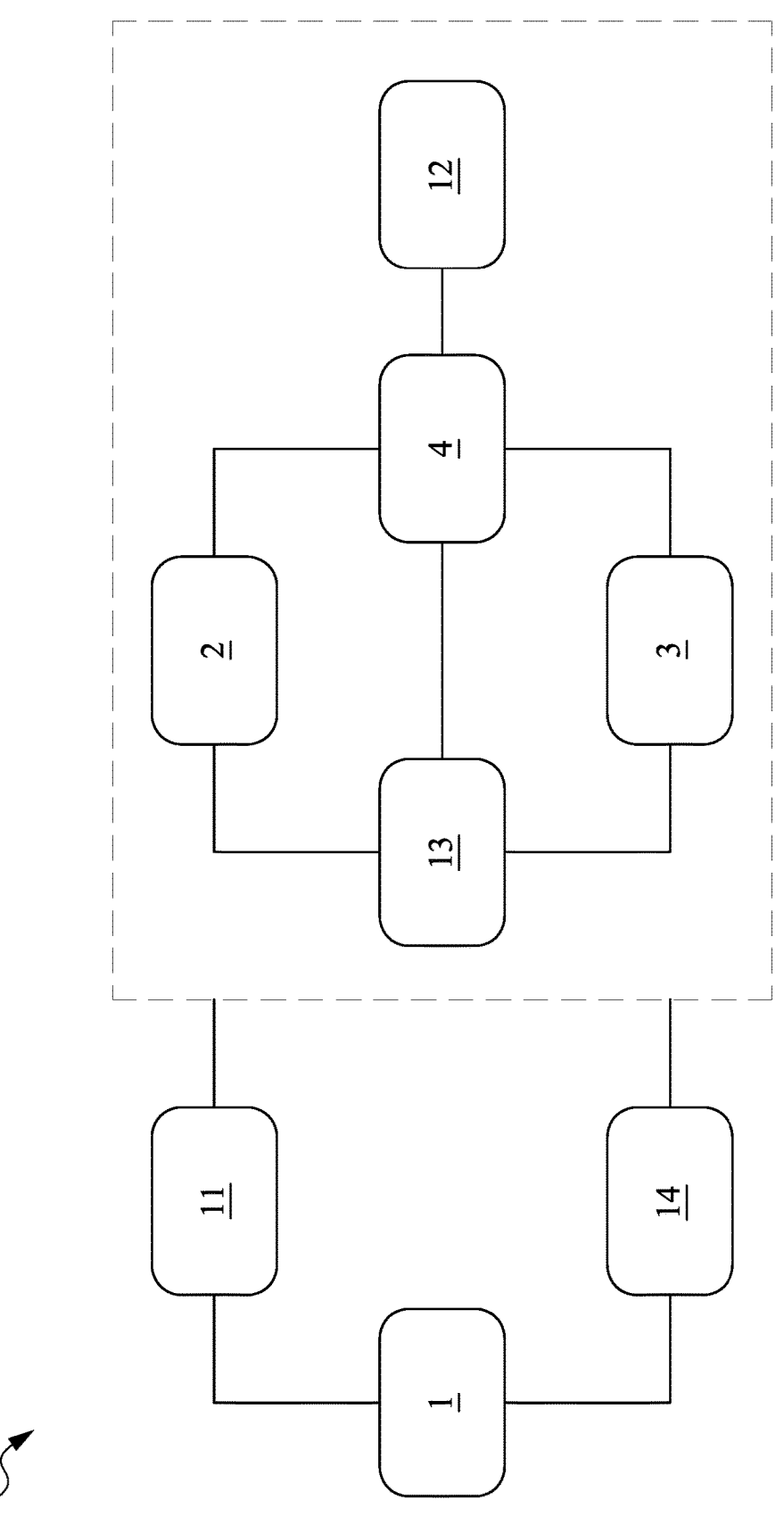
FIG. 2 is a block diagram of the detection apparatus in accordance with an embodiment of the instant disclosure.

FIG. 2 is a block diagram of the detection apparatus 10, according to some embodiments. As shown in FIG. 2, the gas sensing device 2 may be electrically connected to the spectrum analyzer 4. When the electrodes in the gas sensing device 2 apply the AC electrical signal, the current and voltage responses between these electrodes in the gas sensing device 2 may be transmitted from the gas sensing device 2 to the spectrum analyzer 4. When the spectrum analyzer 4 receives the responses from the gas sensing device 2, the spectrum analyzer 4 may record the responses. Further, the spectrum analyzer 4 may calculate complex impedance values based on these responses and result the impedance spectrum.

The solid sensing device 3 may be electrically connected to the spectrum analyzer 4 as well. When the electrodes in the solid sensing device 3 apply the AC electrical signal, the current and voltage responses between these electrodes in the solid sensing device 3 may be transmitted from the gas sensing device 2 to the spectrum analyzer 4. When the spectrum analyzer 4 receives the responses from the solid sensing device 3, the spectrum analyzer 4 may record the responses. Further, the spectrum analyzer 4 may calculate complex impedance values based on these responses and result the impedance spectrum.

Further, the display 12 may be electrically connected to the spectrum analyzer 4. That is, the impedance spectrums generated by the spectrum analyzer 4 may be displayed in the display 12. In some embodiments of the present disclosure, the impedance spectrums generated by the spectrum analyzer 4 may be converted to Nyquist plot and Bode plot to be displayed in the display 12. In some embodiments of the present disclosure, the spectrum analyzer 4 may include a model that includes exhaust gas data and information. When the spectrum analyzer 4 generates the impedance spectrums, the generated impedance spectrums can be matched with the model to directly identify the characteristics of the waste gases. Thus, the display 12 may display the characteristics of the waste gases, such as their composition and concentration.

The DAQ device 13 may be electrically connected to the gas sensing device 2, the solid sensing device 3 and/or the spectrum analyzer 4. That is, the DAQ device 13 may receive and record the current and voltage response from the gas sensing device 2. The DAQ device 13 may receive and record the current and voltage response from the solid sensing device 3. The DAQ device 13 may receive and record the current and voltage response from the gas sensing device 2 and/or the current and voltage response from the solid sensing device 3 through the spectrum analyzer 4. The DAQ device 13 may receive and record the impedance spectrums generated from the spectrum analyzer 4.

Referring to FIG. 2, the gas sensing device 2, the solid sensing device 3, the spectrum analyzer 4, the display 12 and the DAQ device 13 may collectively form a subsystem of the detection apparatus 10. As shown in FIG. 2, the power device 11 is electrically connected to the subsystem of the detection apparatus 10. That is, the power device 11 may provide power to the gas sensing device 2, the solid sensing device 3, the spectrum analyzer 4, the display 12 and/or the DAQ device 13. The controller 14 is electrically connected to the subsystem of the detection apparatus 10. That is, the gas sensing device 2, the solid sensing device 3, the spectrum analyzer 4, the display 12 and/or the DAQ device 13 may be controlled by the controller 14. In addition, the pump 1 may be electrically connected to the power device 11, and thus the power device 11 may provide power to the pump 1. Moreover, the pump 1 may be electrically to the controller 14. That is, the pump 1 may be controlled by the controller 14.

Figure 3A:
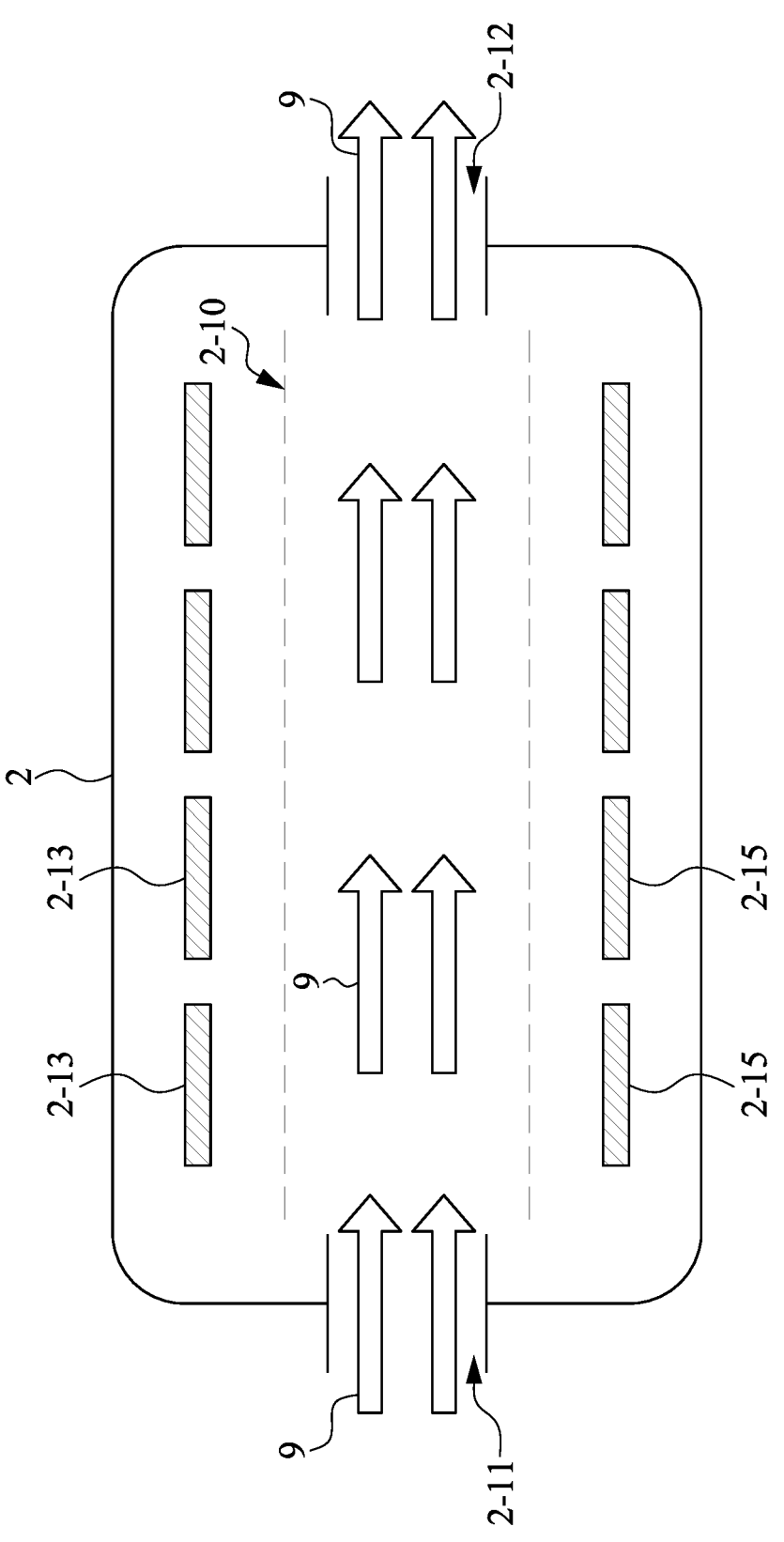
FIG. 3A is a schematic illustration of an embodiment of the gas sensing device of the detection apparatus in accordance with an embodiment of the instant disclosure.

FIG. 3A is a schematic illustration of an embodiment of the gas sensing device 2 of the detection apparatus 10 in accordance with an embodiment of the instant disclosure. As shown in FIG. 3A, the gas sensing device 2 may include an air inlet 2-11 and an air outlet 2-12. The air inlet 2-11 of the gas sensing device 2 may be connected to the pump 1. Thus, waste gases 9 may introduced from the pump 1 into the gas sensing device 2 through the air inlet 2-11. Further, the air outlet 2-12 of the gas sensing device 2 may be connected to the solid sensing device 3. Thus, the waste gases 9 may be discharged from the gas sensing device 2 and flowing into the solid sensing device 3 through the air outlet 2-12. Referring to FIG. 3A, the waste gases 9 may be introduced into the gas sensing device 2 through the air inlet 2-11 and may flow through the gas sensing device 2, and then may flow out of the gas sensing device 2 through the air outlet 2-12, thereby forming a gas flow path 2-10 within the gas sensing device 2. That is, the gas flow path 2-10 may extend from the air inlet 2-11 to the air outlet 2-12.

The gas sensing device 2 may include a plurality of electrodes 2-13 and 2-15. As shown in FIG. 3A, the electrodes 2-13 may be arranged along the gas flow path 2-10 and at one side of the gas flow path 2-10, and the electrodes 2-15 may be arranged along the gas flow path 2-10 and at an opposite side of the gas flow path 2-10. In some embodiments of the present disclosure, the electrodes 2-13 and 2-15 may be substantially disposed in pairs, and the gas flow path 2-10 may extend between the paired electrodes 2-13 and 2-15. That is, the waste gases 9 flowing through the gas flow path 2-10 of the gas sensing device 2 may flow between the paired electrodes 2-13 and 2-15. In some embodiments of the present disclosure, the electrode 2-13, 2-15 may include an electrode sheet and the electrode sheet may be disposed to be substantially parallel to a direction in which the gas flow path 2-10 extends. That is, the electrode 2-13, 2-15 may be substantially parallel to a direction extending from the air inlet 2-11 toward the air outlet 2-12.

When the waste gases 9 is flowing through the gas sensing device 2, a range of AC (alternating current) electrical signals may be applied to the electrodes 2-13 and 2-15. The AC electrical signals may include sinusoidal signals. Then the current and voltage responses between the electrodes 2-13 and 2-15 to the AC electrical signals at each frequency may be obtained. Such response may be considered as the response regarding the waste gases 9 flowing into the gas sensing device 2. The obtained responses may be transmitted to the spectrum analyzer 4, and the spectrum analyzer 4 may measure the responses and generate the impedance spectrums of the waste gases 9 in the gas sensing device 2. These impedance spectrums may provide information about the characteristics of the waste gases 9 in the gas sensing device 2.

The gas sensing device 2 may not include any sensing material capable of electrochemically reacting with the gas. That is, the AC electrical signals from the electrodes 2-13 and 2-15 may be applied directly to the waste gases 9 in the gas sensing device 2. Thus, no electrochemical reaction may occur within the gas sensing device 2 when the AC electrical signals are provided.

Figure 3B:
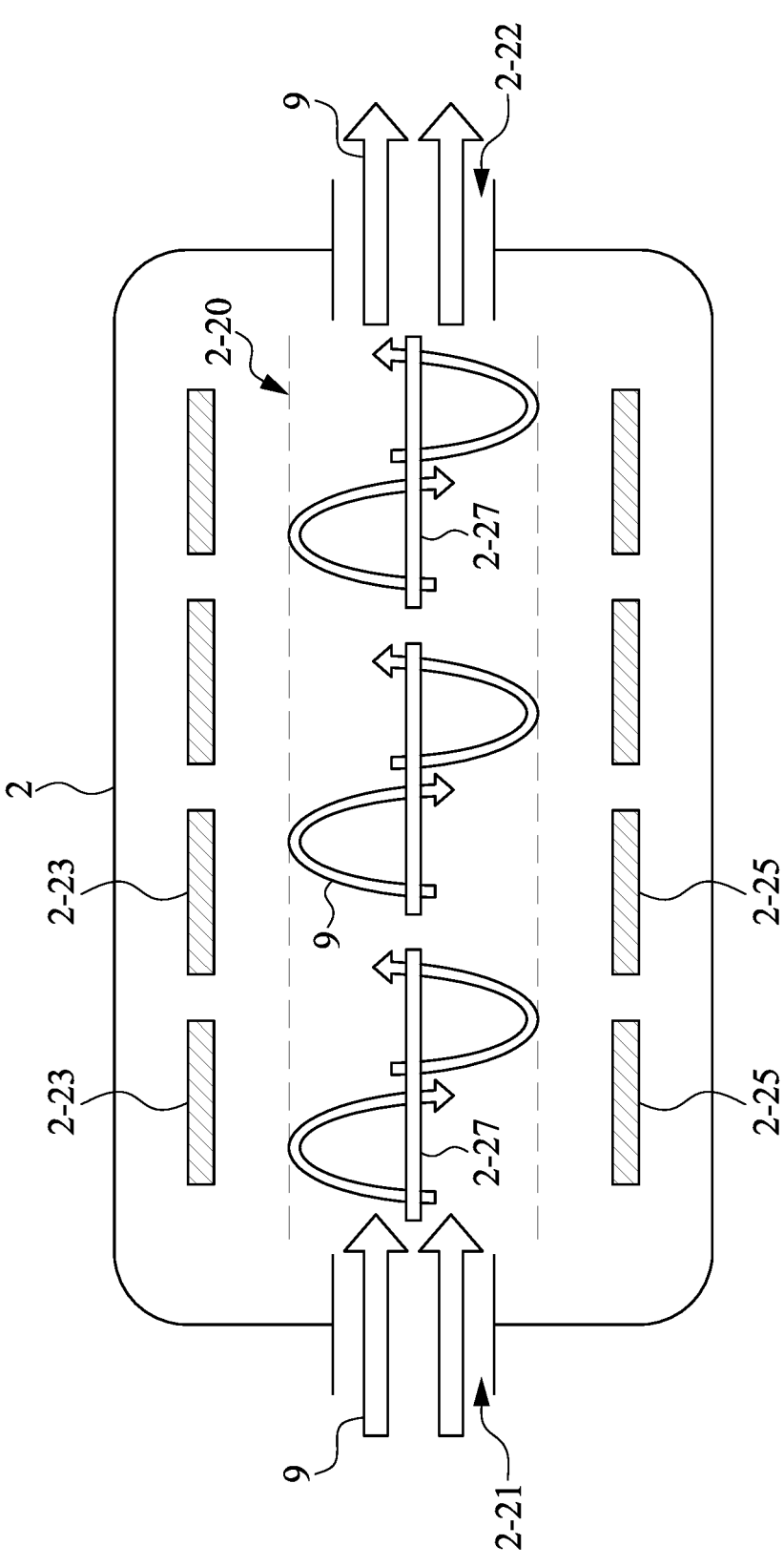
FIG. 3B is a schematic illustration of another embodiment of the gas sensing device of the detection apparatus in accordance with an embodiment of the instant disclosure.

FIG. 3B is a schematic illustration of another embodiment of the gas sensing device 2 of the detection apparatus in accordance with an embodiment of the instant disclosure. As shown in FIG. 3B, the gas sensing device 2 may include an air inlet 2-21 and an air outlet 2-22. The air inlet 2-21 of the gas sensing device 2 may be connected to the pump 1. Thus, waste gases 9 may introduced from the pump 1 into the gas sensing device 2 through the air inlet 2-21. Further, the air outlet 2-22 of the gas sensing device 2 may be connected to the solid sensing device 3. Thus, the waste gases 9 may be discharged from the gas sensing device 2 and flowing into the solid sensing device 3 through the air outlet 2-22. Referring to FIG. 3B, the waste gases 9 may be introduced into the gas sensing device 2 through the air inlet 2-21 and may flow through the gas sensing device 2, and then may flow out of the gas sensing device 2 through the air outlet 2-22, thereby forming a gas flow path 2-20 within the gas sensing device 2. That is, the gas flow path 2-20 may extend from the air inlet 2-21 to the air outlet 2-22.

The gas sensing device 2 may include a plurality of electrodes 2-23 and 2-25. As shown in FIG. 3B, the electrodes 2-23 may be arranged along the gas flow path 2-20 and at one side of the gas flow path 2-20, and the electrodes 2-25 may be arranged along the gas flow path 2-20 and at an opposite side of the gas flow path 2-20. In some embodiments of the present disclosure, the electrodes 2-23 and 2-25 may be substantially disposed in pairs, and the gas flow path 2-20 may extend between the paired electrodes 2-23 and 2-25. That is, the waste gases 9 flowing through the gas flow path 2-20 of the gas sensing device 2 may flow between the paired electrodes 2-23 and 2-25. In some embodiments of the present disclosure, the electrode 2-23, 2-25 may include an electrode sheet and the electrode sheet may be disposed to be substantially parallel to a direction in which the gas flow path 2-20 extends. That is, the electrode 2-23, 2-25 may be substantially parallel to a direction extending from the air inlet 2-21 toward the air outlet 2-22.

The gas sensing device 2 may include a plurality of filters 2-27. The filters 2-27 may be arranged along a direction in which the gas flow path 2-20 extends. The filters 2-27 may be arranged in the gas flow path 2-20. The filters 2-27 may be arranged between the electrodes 2-23 and 2-25. That is, when the waste gases 9 flows through the gas sensing device 2, the waste gases 9 may pass through the filters 2-27. In some embodiments of the present disclosure, the filters 2-27 may be substantially parallel to a direction in which the gas flow path 2-20 extends. That is, the filters 2-27 may be substantially to a direction extending from the air inlet 2-21 toward the air outlet 2-222. Even though the filters 2-27 may be arranged in such a way, the waste gases 9 may still pass through the filters 2-27. In some embodiments of the present disclosure, a pore size of the filter 2-27 may be large enough to allow solid in the waste gases 9 to pass through. As above mentioned, the waste gases 9 may include acid and alkaline gases, and the acid and alkaline gases may include salt solids. The size of the pores of the filter 2-27 may be not sufficient to collect the salt solids, which can pass through the pores of the filter 2-27 along with the waste gases 9.

When the waste gases 9 is flowing into the gas sensing device 2 and passing through the filters 2-27, a range of AC (alternating current) electrical signals may be applied to the electrodes 2-23 and 2-25. The AC electrical signals may include sinusoidal signals. Then the current and voltage responses caused by the waste gases 9 passing through the filter 2-27 and/or the filters 2-27 to the AC electrical signals at each frequency may be obtained. Such response may be considered as the response regarding the waste gases 9 passing through the filters 2-27 in the gas sensing device 2. The obtained responses may be transmitted to the spectrum analyzer 4, and the spectrum analyzer 4 may measure the responses and generate the impedance spectrums of the waste gases 9 passing through the filters 2-27 in the gas sensing device 2. These impedance spectrums may provide information about the characteristics of the waste gases 9 in the gas sensing device 2.

The gas sensing device 2 may not include any sensing material capable of electrochemically reacting with the gas. That is, the AC electrical signals from the electrodes 2-23 and 2-25 may be applied directly to the waste gases 9 passing through the filters 2-27 and/or the filters 2-27. Thus, no electrochemical reaction may occur within the gas sensing device 2 when the AC electrical signals are provided.

Figure 3C:
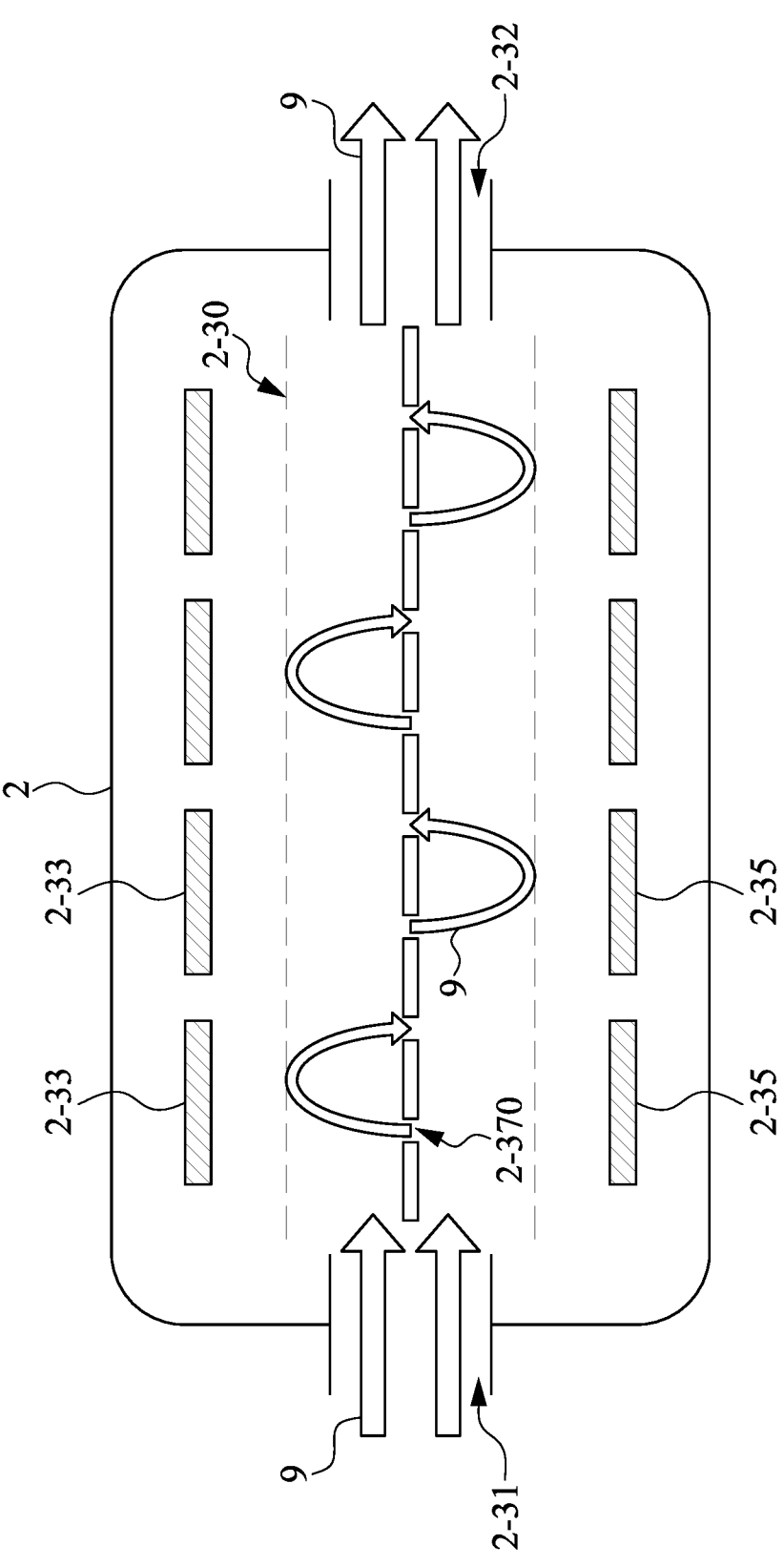
FIG. 3C is a schematic illustration of another embodiment of the gas sensing device of the detection apparatus in accordance with an embodiment of the instant disclosure.

FIG. 3C is a schematic illustration of another embodiment of the gas sensing device 2 of the detection apparatus in accordance with an embodiment of the instant disclosure. As shown in FIG. 3C, the gas sensing device 2 may include an air inlet 2-31 and an air outlet 2-32. The air inlet 2-31 of the gas sensing device 2 may be connected to the pump 1. Thus, waste gases 9 may introduced from the pump 1 into the gas sensing device 2 through the air inlet 2-31. Further, the air outlet 2-32 of the gas sensing device 2 may be connected to the solid sensing device 3. Thus, the waste gases 9 may be discharged from the gas sensing device 2 and flowing into the solid sensing device 3 through the air outlet 2-32. Referring to FIG. 3C, the waste gases 9 may be introduced into the gas sensing device 2 through the air inlet 2-31 and may flow through the gas sensing device 3, and then may flow out of the gas sensing device 2 through the air outlet 2-32, thereby forming a gas flow path 2-30 within the gas sensing device 2. That is, the gas flow path 2-30 may extend from the air inlet 2-31 to the air outlet 2-32.

The gas sensing device 2 may include a plurality of electrodes 2-33 and 2-35. As shown in FIG. 3C, the electrodes 2-33 may be arranged along the gas flow path 2-30 and at one side of the gas flow path 2-30, and the electrodes 2-35 may be arranged along the gas flow path 2-30 and at an opposite side of the gas flow path 2-30. In some embodiments of the present disclosure, the electrodes 2-33 and 2-35 may be substantially disposed in pairs, and the gas flow path 2-30 may extend between the paired electrodes 2-33 and 2-35. That is, the waste gases 9 flowing through the gas flow path 2-30 of the gas sensing device 2 may flow between the paired electrodes 2-33 and 2-35. In some embodiments of the present disclosure, the electrode 2-33, 2-35 may include an electrode sheet and the electrode sheet may be disposed to be substantially parallel to a direction in which the gas flow path 2-30 extends. That is, the electrode 2-33, 2-35 may be substantially parallel to a direction extending from the air inlet 2-31 toward the air outlet 2-32.

The gas sensing device 2 may include a plurality of through holes 2-370. The through holes 2-370 may be arranged in the gas flow path 2-30. The through holes 2-370 may be arranged between the electrodes 2-33 and 2-35. That is, when the waste gases 9 flows through the gas sensing device 2, the waste gases 9 may pass through the through holes 2-27. In some embodiments of the present disclosure, a size of the through hole 2-370 may be large enough to allow solids in the waste gases 9 to pass through. As above mentioned, the waste gases 9 may include acid and alkaline gases, and the acid and alkaline gases may include salt solids. The size of the through hole 2-370 may not block the salt solids and the salt solids can pass through the through holes 2-370 along with the waste gases 9.

When the waste gases 9 is flowing into the gas sensing device 2 and passing through the through holes 2-370, a range of AC (alternating current) electrical signals may be applied to the electrodes 2-33 and 2-35. The AC electrical signals may include sinusoidal signals. Then the current and voltage responses caused by the waste gases 9 and/or the through hole 2-370 to the AC electrical signals at each frequency may be obtained. Such response may be considered as the response regarding the waste gases 9 passing through the through holes 2-370 in the gas sensing device 2. The obtained responses may be transmitted to the spectrum analyzer 4, and the spectrum analyzer 4 may measure the responses and generate the impedance spectrums of the waste gases 9 passing through the through holes 2-370 in the gas sensing device 2. These impedance spectrums may provide information about the characteristics of the waste gases 9 in the gas sensing device 2.

The gas sensing device 2 may not include any sensing material capable of electrochemically reacting with the gas. That is, the AC electrical signals from the electrodes 2-33 and 2-35 may be applied directly to the waste gases 9 passing through the through holes 2-370 and/or the though holes 2-370. Thus, no electrochemical reaction may occur within the gas sensing device 2 when the AC electrical signals are provided.

Figure 4A:
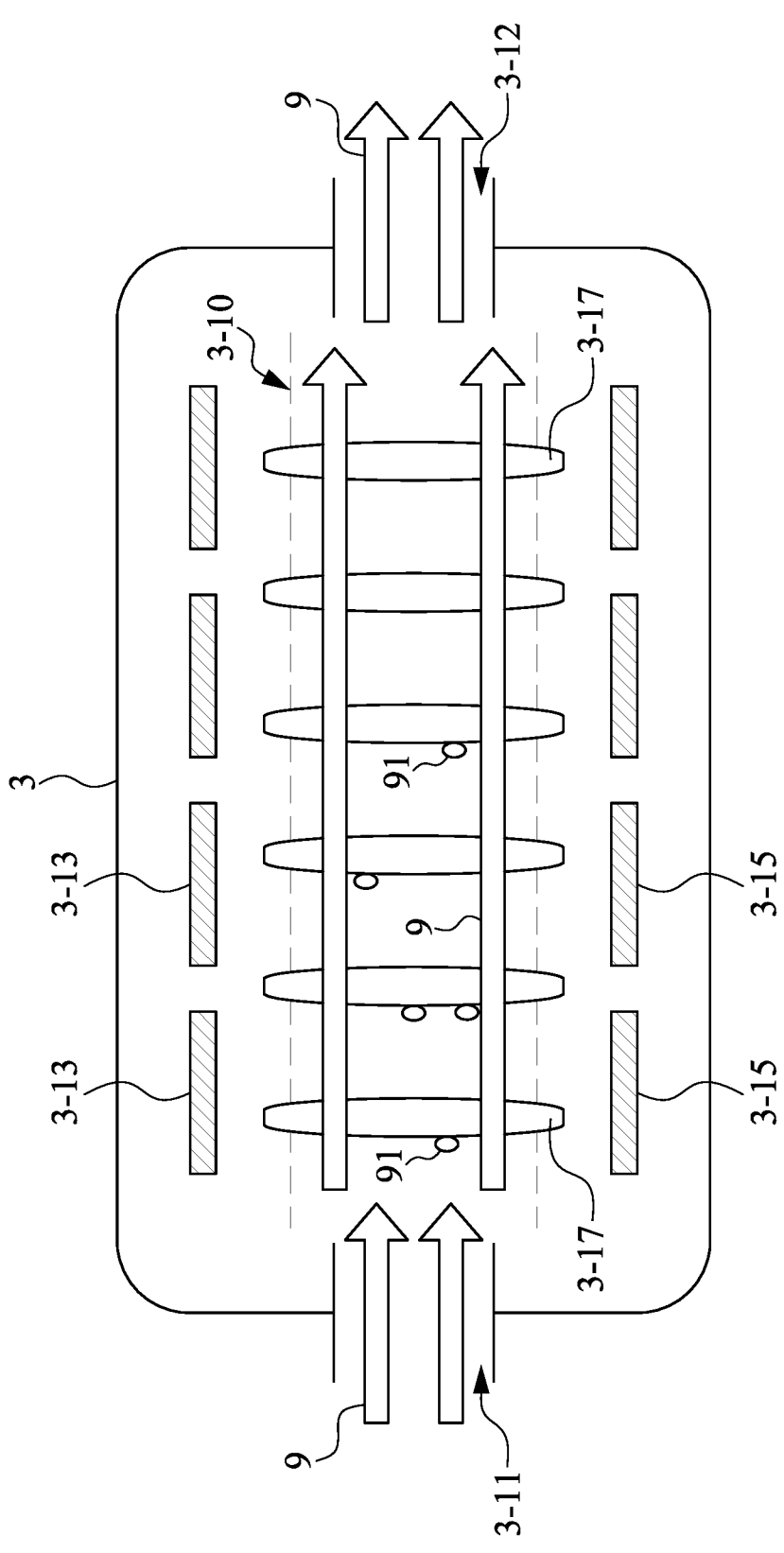
FIG. 4A is a schematic illustration of an embodiment of the solid sensing device of the detection apparatus in accordance with an embodiment of the instant disclosure.

FIG. 4A is a schematic illustration of an embodiment of the solid sensing device 3 of the detection apparatus 10 in accordance with an embodiment of the instant disclosure. As shown in FIG. 4A, the solid sensing device 3 may include an air inlet 3-11 and an air outlet 3-12. The air inlet 3-11 of the solid sensing device 3 may be connected to the air outlet 2-11 or 2-21 of the gas sensing device 2. Thus, the waste gases 9 may flow out of the gas sensing device 2 and then flow into the solid sensing device 3 through the air inlet 3-11. In some embodiments of the present disclosure, the air outlet 3-12 of the solid sensing device 3 may be connected to the air outlet 102 of the detection apparatus 10. In some embodiments of the present disclosure, the air outlet 3-12 of the solid sensing device 3 may include the air outlet 102 of the detection apparatus 10. That is, when the waste gases 9 flow through the air outlet 3-12 of the solid sensing device 3, the waste gases 9 may be expelled from the detection apparatus 10. Referring to FIG. 4A, the waste gases 9 may be introduced into the solid sensing device 3 through the air inlet 3-11 and may flow through the solid sensing device 3, and then may flow out of the solid sensing device 3 through the air outlet 3-12, thereby forming a gas flow path 3-10 within the solid sensing device 3. That is, the gas flow path 3-10 may extend from the air inlet 3-11 to the air outlet 3-12.

The solid sensing device 3 may include a plurality of electrodes 3-13 and 3-15. As shown in FIG. 4A, the electrodes 3-13 may be arranged along the gas flow path 3-10 and at one side of the gas flow path 3-10, and the electrodes 3-15 may be arranged along the gas flow path 3-10 and at an opposite side of the gas flow path 3-10. In some embodiments of the present disclosure, the electrodes 3-13 and 3-15 may be substantially disposed in pairs, and the gas flow path 3-10 may extend between the paired electrodes 3-13 and 3-15. That is, the waste gases 9 flowing through the gas flow path 3-10 of the solid sensing device 3 may flow between the paired electrodes 3-13 and 3-15. In some embodiments of the present disclosure, the electrode 3-13, 3-15 may include an electrode sheet and the electrode sheet may be disposed to be substantially parallel to a direction in which the gas flow path 3-10 extends. That is, the electrode 3-13, 3-15 may be substantially parallel to a direction extending from the air inlet 3-11 toward the air outlet 3-12.

The solid sensing device 3 may include a plurality of filters 3-17. The filters 3-17 may be arranged between the paired electrodes 3-13 and 3-15. Further, the gas flow path 3-10 may pass through the filters 3-17. Thus, the waste gases 9 flowing in the gas flow path 3-10 may pass through the filter 3-17. In some embodiments of the present disclosure, the filter 3-17 may be substantially perpendicular to the direction in which the gas flow path 3-10 extends. That is the filter 3-17 may be substantially to perpendicular to the direction extending from the air inlet 3-11 toward the air outlet 3-12. In some embodiments of the present disclosure, a pore size of the filter 3-17 is sufficient to block solid in the waste gases 9 from passing through. As above mentioned, the waste gases 9 may include acid and alkaline gases, and the acid and alkaline gases may include salt solids. The filter 3-17 may collect the salt solids and retain the salt solids on the filter 3-17 when the waste gases 9 passes through the filter 3-17.

When the waste gases 9 is flowing into the solid sensing device 3 and passing through the filters 3-17 and the solids 91 in the waste gases 9 are retained on the filters 3-17, a range of AC (alternating current) electrical signals may be applied to the electrodes 3-13 and 3-15. The AC electrical signals may include sinusoidal signals. Then the current and voltage responses caused by the solids 91 on the filters 3-17 to the AC electrical signals at each frequency may be obtained. Such response may be considered as the response regarding the solids 91 in the waste gases 9 in the solid sensing device 3. The obtained responses may be transmitted to the spectrum analyzer 4, and the spectrum analyzer 4 may measure the responses and generate the impedance spectrums (of the solids 91) of the waste gases 9 passing through the filters 3-17 in the solid sensing device 3. These impedance spectrums may provide information about the characteristics of the waste gases 9 in the solid sensing device 3.

In addition, when the solids 91 in the waste gases 9 are blocked by the filters 3-17, the waste gases 9 may pass through the filters 3-17 at the same time. Thus, when applying a range of AC (alternating current) electrical signals to the electrodes 3-13 and 3-15, the current and voltage responses caused by the waste gases 9 passing through the filters 3-17 to the AC electrical signals at each frequency may be obtained as well. Such response may be considered as the response regarding the waste gases 9 passing through the filters 3-17 in the solid sensing device 3. The obtained responses may be transmitted to the spectrum analyzer 4, and the spectrum analyzer 4 may measure the responses and generate the impedance spectrums of the waste gases 9 passing through the filters 3-17 in the solid sensing device 3. These impedance spectrums may provide information about the characteristics of the waste gases 9 in the solid sensing device 3.

The solid sensing device 3 may not include any sensing material capable of electrochemically reacting with the filters 3-17 and/or the solids 91 on the filters 3-17 and/or the waste gases 9 passing through the filters 3-17. That is, the AC electrical signals from the electrodes 3-13 and 3-15 may be applied directly to the filters 3-17 and/or the solids 91 on the filters 3-17 and/or the waste gases 9 passing through the filters 3-17. Thus, no electrochemical reaction may occur within the solid sensing device 3 when the AC electrical signals are provided.

Figure 4B:
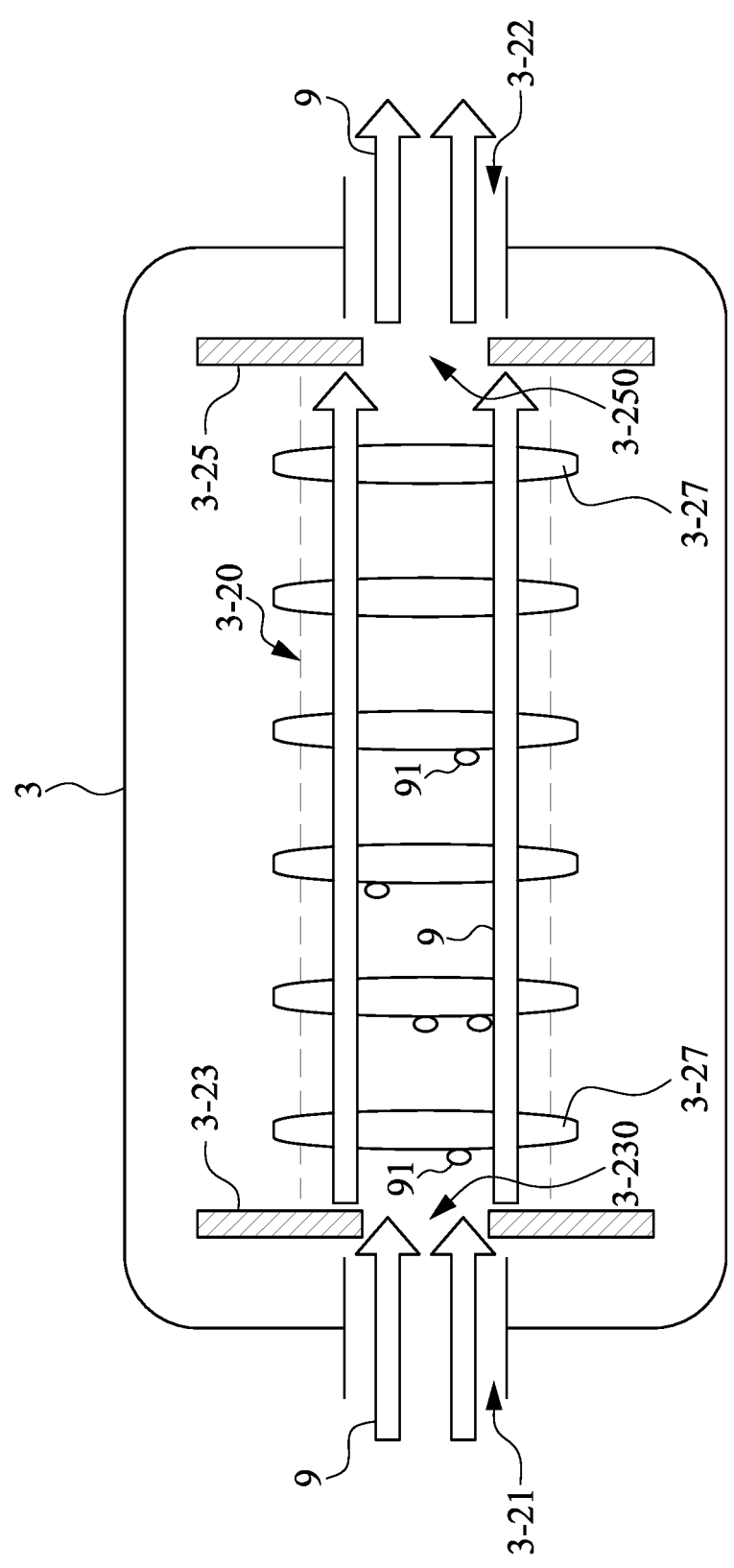
FIG. 4B is a schematic illustration of another embodiment of the solid sensing device of the detection apparatus in accordance with an embodiment of the instant disclosure.

FIG. 4B is a schematic illustration of another embodiment of the solid sensing device 3 of the detection apparatus 10 in accordance with an embodiment of the instant disclosure. As shown in FIG. 4B, the solid sensing device 3 may include an air inlet 3-21 and an air outlet 3-22. The air inlet 3-21 of the solid sensing device 3 may be connected to the air outlet 2-11 or 2-21 of the gas sensing device 2. Thus, the waste gases 9 may flow out of the gas sensing device 2 and then flow into the solid sensing device 3 through the air inlet 3-11. In some embodiments of the present disclosure, the air outlet 3-22 of the solid sensing device 3 may be connected to the air outlet 102 of the detection apparatus 10. In some embodiments of the present disclosure, the air outlet 3-22 of the solid sensing device 3 may include the air outlet 102 of the detection apparatus 10. That is, when the waste gases 9 flow through the air outlet 3-22 of the solid sensing device 3, the waste gases 9 may be expelled from the detection apparatus 10. Referring to FIG. 4B, the waste gases 9 may be introduced into the solid sensing device 3 through the air inlet 3-21 and may flow through the solid sensing device 3, and then may flow out of the solid sensing device 3 through the air outlet 3-22, thereby forming a gas flow path 3-20 within the solid sensing device 3. That is, the gas flow path 3-20 may extend from the air inlet 3-21 to the air outlet 3-22.

The solid sensing device 3 may include a pair of electrodes 3-23 and 3-25. As shown in FIG. 4B, the electrode 3-23 may be arranged to be adjacent to the air inlet 3-21 of the solid sensing device 3, and the electrode 3-25 may be arranged to be adjacent to the air outlet 3-22 of the solid sensing device 3. That is, the electrodes 3-23 and 3-25 are respectively arranged at two opposite ends of the gas flow path 3-20. In some embodiments of the present disclosure, the electrode 3-23, 3-25 may be substantially perpendicular to the direction in which the gas flow path 3-20 extends. That is, the electrode 3-23, 3-25 may be substantially to perpendicular to the direction extending from the air inlet 3-21 toward the air outlet 3-22. In some embodiments of the present disclosure, the electrode 3-23 may include a through-hole 3-230. The waste gases 9 flowing through the air inlet 3-21 may pass through the through-hole 3-230 of the electrode 3-23 and flow into the gas flow path 3-20. In some embodiments of the present disclosure, the electrode 3-25 may include a through-hole 3-250. The waste gases 9 may pass through the through-hole 3-250 of the electrode 3-25 and flow out of the solid sensing device 3 through the air outlet 3-22.

The solid sensing device 3 may include a plurality of filters 3-27. The filters 3-27 may be arranged between the pair of the electrodes 3-23 and 3-25. Further, the gas flow path 3-20 may pass through the filters 3-27. Thus, the waste gases 9 flowing in the gas flow path 3-20 may pass through the filter 3-27. In some embodiments of the present disclosure, the filter 3-27 may be substantially perpendicular to the direction in which the gas flow path 3-20 extends. That is, the filter 3-27 may be substantially to perpendicular to the direction extending from the air inlet 3-21 toward the air outlet 3-22. In some embodiments of the present disclosure, a pore size of the filter 3-27 is sufficient to block solid in the waste gases 9 from passing through. As above mentioned, the waste gases 9 may include acid and alkaline gases, and the acid and alkaline gases may include salt solids. The filter 3-27 may collect the salt solids and retain the salt solids on the filter 3-27 when the waste gases 9 passes through the filter 3-27.

When the waste gases 9 is flowing into the solid sensing device 3 and passing through the filters 3-27 and the solids 91 in the waste gases 9 are retained on the filters 3-27, a range of AC (alternating current) electrical signals may be applied to the electrodes 3-23 and 3-25. The AC electrical signals may include sinusoidal signals. Then the current and voltage responses caused by the solids 91 on the filters 3-27 to the AC electrical signals at each frequency may be obtained. Such response may be considered as the response regarding the solids 91 in the waste gases 9 in the solid sensing device 3. The obtained responses may be transmitted to the spectrum analyzer 4, and the spectrum analyzer 4 may measure the responses and generate the impedance spectrums (of the solids 91) of the waste gases 9 passing through the filters 3-27 in the solid sensing device 3. These impedance spectrums may provide information about the characteristics of the waste gases 9 in the solid sensing device 3.

In addition, when the solids 91 in the waste gases 9 are blocked by the filters 3-27, the waste gases 9 may pass through the filters 3-27 at the same time. Thus, when applying a range of AC (alternating current) electrical signals to the electrodes 3-23 and 3-25, the current and voltage responses caused by the waste gases 9 passing through the filters 3-27 to the AC electrical signals at each frequency may be obtained as well. Such response may be considered as the response regarding the waste gases 9 passing through the filters 3-27 in the solid sensing device 3. The obtained responses may be transmitted to the spectrum analyzer 4, and the spectrum analyzer 4 may measure the responses and generate the impedance spectrums of the waste gases 9 passing through the filters 3-27 in the solid sensing device 3. These impedance spectrums may provide information about the characteristics of the waste gases 9 in the solid sensing device 3.

The solid sensing device 3 may not include any sensing material capable of electrochemically reacting with the filters 3-27 and/or the solids 91 on the filters 3-27 and/or the waste gases 9 passing through the filters 3-27. That is, the AC electrical signals from the electrodes 3-23 and 3-25 may be applied directly to the filters 3-27 and/or the solids 91 on the filters 3-27 and/or the waste gases 9 passing through the filters 3-27. Thus, no electrochemical reaction may occur within the solid sensing device 3 when the AC electrical signals are provided.

FIG. 5 is a flow chart representing a method for operating the detection apparatus in accordance with an embodiment of the present disclosure.

In Operation 51, waste gases 9 generated from semiconductor manufacturing may be introduced into the detection apparatus 10. In some embodiments of the present disclosure, the waste gases 9 may include acid and alkaline gases. In some embodiments of the present disclosure, the waste gases 9 may be introduced into the detection apparatus 10 by the pump 1 of the detection apparatus 10. In some embodiments of the present disclosure, the waste gases 9 may be introduced from a local scrubber system. In some embodiments of the present disclosure, the waste gases 9 may be introduced from a central scrubber system. In some embodiments of the present disclosure, the waste gases 9 may be introduced from a chimney of the factory.

In operation 52, the waste gases 9 may be introduced into the gas sensing device 2. In some embodiments of the present disclosure, the pump 1 may introduce the waste gases 9 into the gas sensing device 2.

In operation 53, a range of AC (alternating current) electrical signals may be applied to the electrodes 2-13, 2-15, 2-23, 2-25 in the gas sensing device 2 when the waste gases 9 flow into the gas sensing device 2. In some embodiments of the present disclosure, the waste gases 9 may directly flow between the electrodes 2-13, 2-15, and the current and voltage responses between the electrodes 2-13 and 2-15 may be obtained when apply the AC electrical signals to the electrodes 2-13, 2-15. In some embodiments of the present disclosure, the waste gases 9 may pass through the filters 2-27 between the electrodes 2-23, 2-25, and the current and voltage responses caused by the filters 2-27 may be obtained when apply the AC electrical signals to the electrodes 2-23, 2-25. That is, the responses regarding the waste gases 9 in the gas sensing device 2 may be obtained after the AC electrical signals is applied. In some embodiments of the present disclosure, the obtained responses may be transmitted from the gas sensing device to the spectrum analyzer 4.

In operation 54, the waste gases 9 may flow out of the gas sensing device 2 and flow into the solid sensing device 3.

In operation 55, a range of AC (alternating current) electrical signals may be applied to the electrodes 3-13, 3-15, 3-23, 3-25 in the solid sensing device 3 when the waste gases 9 flow into the solid sensing device 3. In some embodiments of the present disclosure, the solids 91 in the waste gases 9 flowing into the solid sensing device 3 may be collected by the filters 3-17, 3-27, and the current and voltage responses caused by the filters 3-17, 3-27 may be obtained when apply the AC electrical signals to the electrodes 3-13, 3-15 3-23, 3-25. That is, the responses regarding the solids 91 in the waste gases 9 in the solid sensing device 3 may be obtained after the AC electrical signals is applied. In some embodiments of the present disclosure, the waste gases 9 flowing into the solid sensing device 3 may pass through the filters 3-17, 3-27, and the current and voltage responses caused by the filters 3-17, 3-27 may be obtained when apply the AC electrical signals to the electrodes 3-13, 3-15 3-23, 3-25. That is, the responses regarding the waste gases 9 in the solid sensing device 3 may be obtained after the AC electrical signals is applied. In some embodiments of the present disclosure, the obtained responses may be transmitted from the solid sensing device 3 to the spectrum analyzer 4.

In operation 56, the spectrum analyzer 4 may measure the responses and generate the impedance spectrums. In some embodiments of the present disclosure, the spectrum analyzer 4 may measure the responses from the gas sensing device 2 and generate the impedance spectrums of the waste gases 9 in the gas sensing device 2. In some embodiments of the present disclosure, the spectrum analyzer 4 may measure the responses from the solid sensing device 3 and generate the impedance spectrums of the solids 91 in the waste gases 9 in the solid sensing device 3 and/or the impedance spectrums of the waste gases 9 in the solid sensing device 3. The users may identify the characteristics of the waste gases 9 based on the impedance spectrums generated by the spectrum analyzer 4.

In operation 57, the waste gases 9 may be discharged from the detection apparatus 10. In some embodiments of the present disclosure, the waste gases 9 discharged from the detection apparatus 10 may be recollected.

Figure 6:
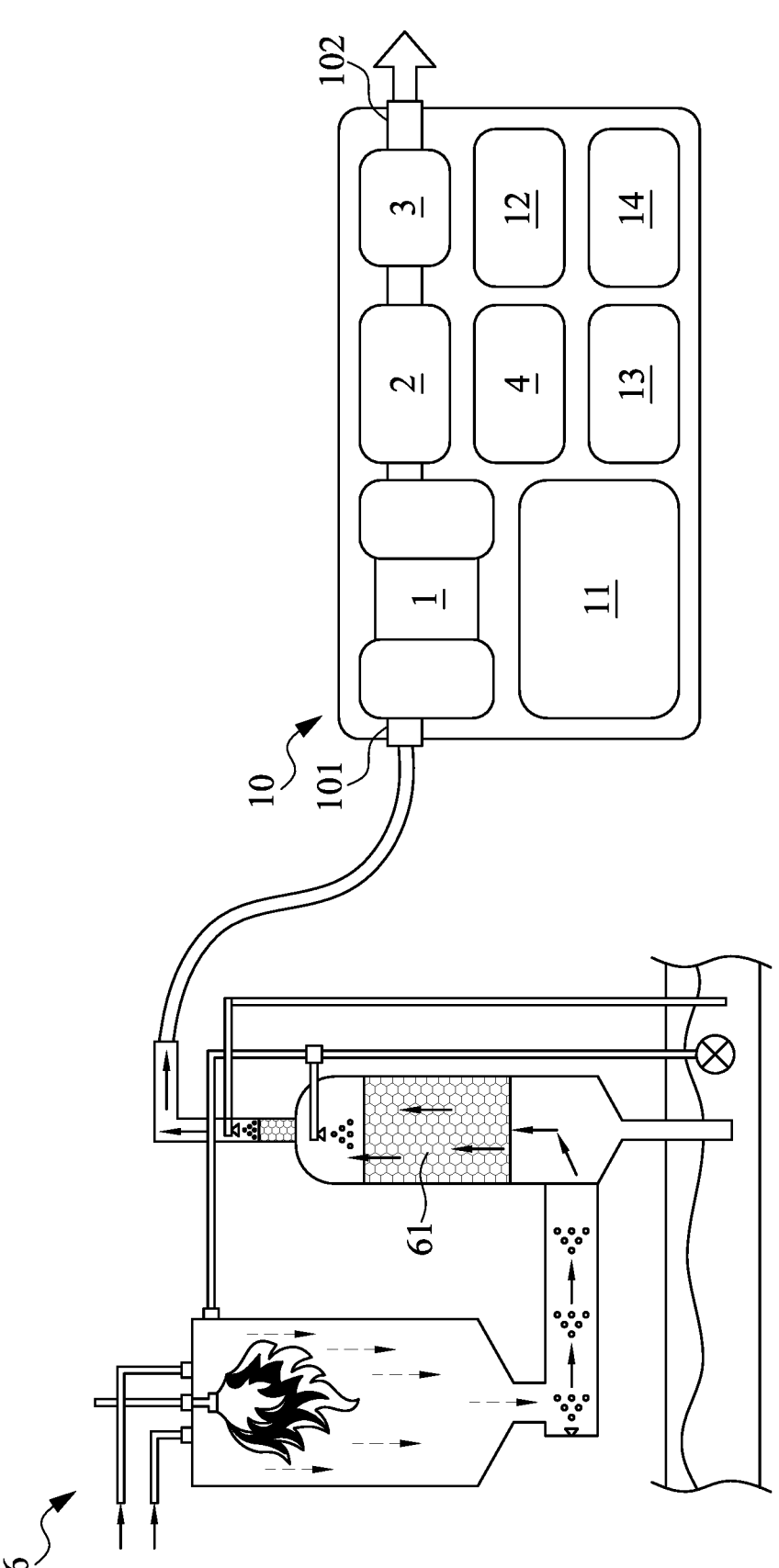
FIG. 6 illustrates a state of use of the detection apparatus in accordance with an embodiment of the instant disclosure.

FIG. 6 illustrates a state of use of the detection apparatus 10 in accordance with an embodiment of the instant disclosure. As shown in FIG. 6, the detection apparatus 10 may be located at the local scrubber system 6. In some embodiments of the present disclosure, the detection apparatus 10 may connected to the fab exhaust of the local scrubber system 6 and pump the waste gas which has passed through the scrubber 61 into the detection apparatus 10. Users may learn about the characteristics of the waste gases emitted by the local scrubber system 6 through the detection apparatus 10. Further, the processing efficiency of the local scrubber system 6 may be determined.

Figure 7:
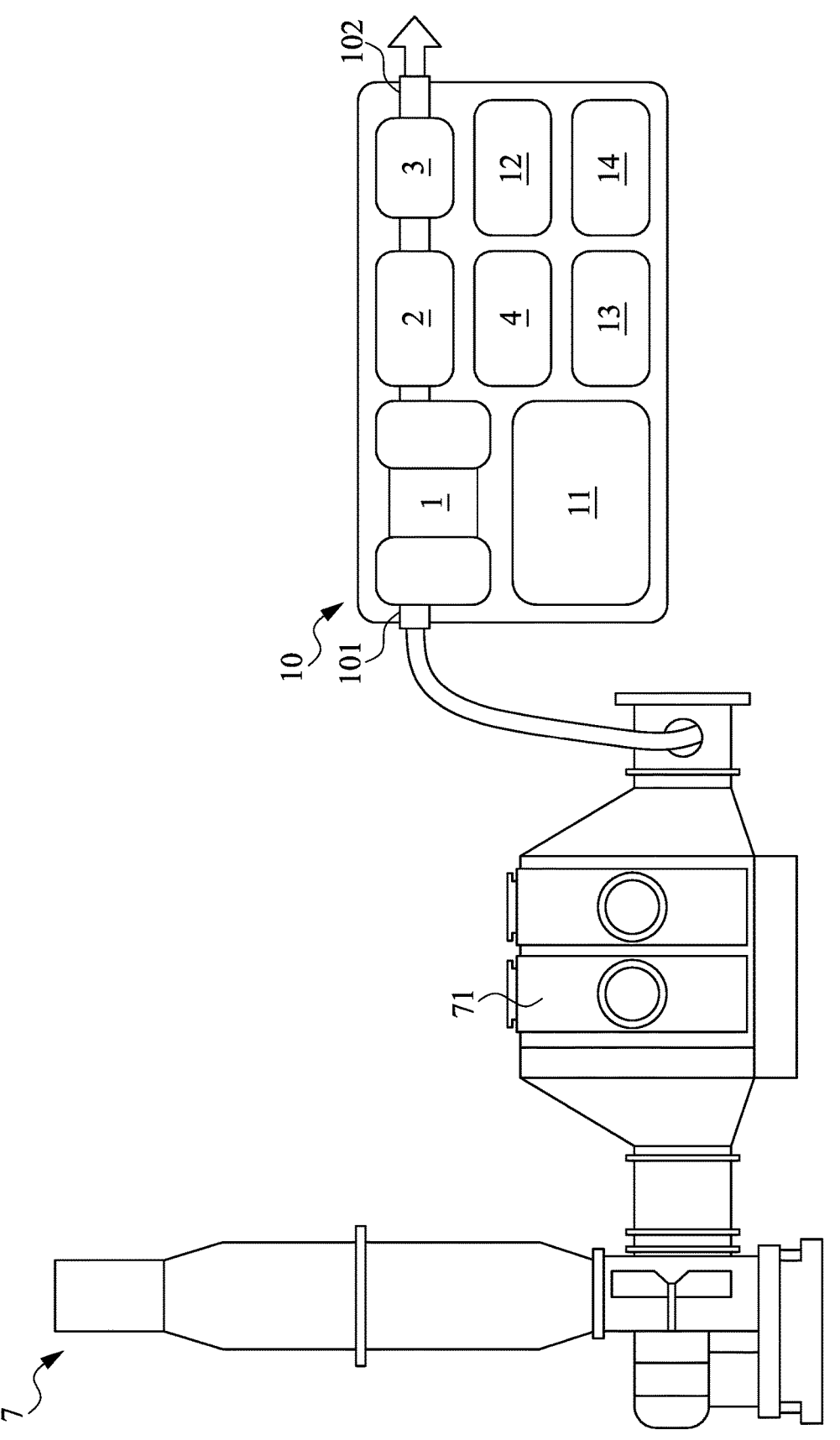
FIG. 7 illustrates another state of use of the detection apparatus in accordance with an embodiment of the instant disclosure.

FIG. 7 illustrates another state of use of the detection apparatus 10 in accordance with an embodiment of the instant disclosure. As shown in FIG. 7, the detection apparatus 10 may be located at the central scrubber system 7. In some embodiments of the present disclosure, the detection apparatus 10 may connected to the fab exhaust of the central scrubber system 7 and pump the waste gas which has passed through the scrubber 71 into the detection apparatus 10. Users may learn about the characteristics of the waste gases emitted by the central scrubber system 7 through the detection apparatus 10. Further, the processing efficiency of the local scrubber system 7 may be determined.

Figure 8:
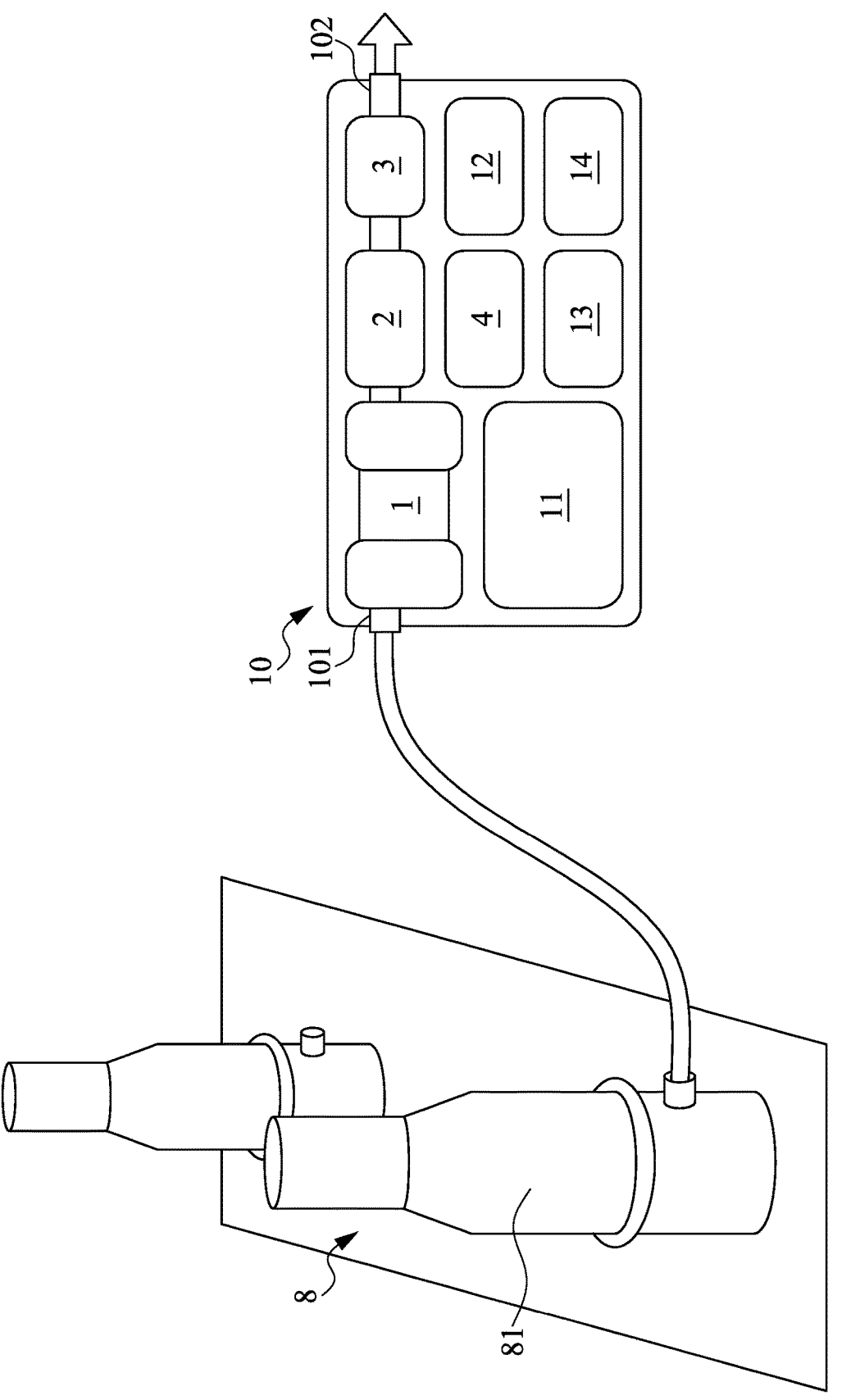
FIG. 8 illustrates another state of use of the detection apparatus in accordance with an embodiment of the instant disclosure.

FIG. 8 illustrates another state of use of the detection apparatus 10 in accordance with an embodiment of the instant disclosure. As shown in FIG. 8, the detection apparatus 10 may be located at the chimney platform 8. In some embodiments of the present disclosure, the detection apparatus 10 may connected to the chimney 81 of the chimney platform 8 and pump the waste gas from the chimney 8 into the detection apparatus 10. Users may learn about the characteristics of the waste gases emitted by the chimney 81 through the detection apparatus 10 and determine whether the waste gases emitted by the chimney 81 can meet the requirement.

It will be appreciated that in the forgoing apparatus, the waste gases generated from semiconductor manufacturing could be detected and/or identified in real-time. Users may use the detection application to monitor emissions from the semiconductor manufacturing tool and/or the semiconductor fabrication plant and infer or identify characteristics of the emissions, such as their composition and concentration in real-time. That is, the users may determine the processing efficiency of the local or central scrubber system and learn whether the emissions meet the requirement of Net Zero Emissions.

According to one embodiment of the present disclosure, a detection apparatus, comprises: a first sensing device, a second sensing device in fluid communication with the first sensing device and a spectrum analyzer electrically connected to the first sensing device and the second sensing device. The first sensing device includes a pair of first electrodes configured to provide a first alternating current signal directly to a gas flowing into the first sensing device. The second sensing device includes a first filter configured to capture a solid in the gas flowing into the second sensing device and a pair of second electrodes configured to provide a second alternating current signal directly to the first filter with the solid captured by the first filter.

According to another embodiment of the present disclosure, a detection apparatus, comprises: a first device configured to apply a first alternating current signal to obtain a first response associated with a gas flowing through the first device, wherein the first device is free of a sensing material capable of electrochemically reacting with the gas flowing through the first device; a second device configured to apply a second alternating current signal to obtain a second response associated with a solid in the gas flowing through the second device, wherein the second device is free of a sensing material capable of electrochemically reacting with the solid in the gas flowing through the second device; and an analyzer configured to receive the first response and the second response and generate at least one impedance spectrum based on the first response and the second response.

According to one embodiment of the present disclosure, a method of detecting a characteristic of a gas, comprises: providing the gas flowing into a first device; applying a first alternating current signal directly to the gas in the first device so as to obtain a first response; providing the gas flowing from the first device into a second device; applying a second alternating current signal directly to a first filter disposed in the second device and configured to collect a solid in the gas in the second device so as to obtain a second response; and generating at least one impedance spectrum based on the first response and the second response.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A detection apparatus for detecting a gas generated from semiconductor manufacturing, comprising:
   a first sensing device, which comprises a pair of first electrodes configured to supply a first alternating current signal directly to the gas flowing into the first sensing device;
   a second sensing device, which is in fluid communication with the first sensing device and comprises a first filter configured to capture a solid in the gas flowing into the second sensing device and a pair of second electrodes configured to supply a second alternating current signal directly to the first filter with the solid captured by the first filter; and
   a spectrum analyzing device electrically connected to the first sensing device and the second sensing device;
   wherein the gas comprises an acid gas and an alkaline gas, and wherein the solid comprises a salt solid.

2. The detection apparatus of claim 1, wherein the first sensing device comprises a first air inlet and a first air outlet and the second sensing device comprises a second inlet and a second outlet, and wherein the first inlet of the sensing device is configured to introduce the gas into the first sensing device, and wherein the first air outlet of the first sensing device is connected to the second inlet of the second sensing device, and wherein second outlet of the second sensing device is configured to release the gas from the second sensing device.

3. The detection apparatus of claim 2, wherein the first sensing device comprises a second filter arranged between the pair of the first electrodes and being substantially parallel to a direction extending from the first air inlet of the first sensing device toward the first air outlet of the first sensing device, and wherein the first alternating current signal is directly supplied to the filter and the gas passing through the second filter.

4. The detection apparatus of claim 2, wherein the first filter is substantially perpendicular to a direction extending from the second air inlet of the second sensing device toward the second air outlet of the second sensing device and arranged between the pair of the pair of second electrodes.

5. The detection apparatus of claim 4, wherein the pair of the second electrodes are arranged to be substantially parallel to a direction extending from the second air inlet of the second sensing device toward the second air outlet of the second sensing device.

6. The detection apparatus of claim 4, wherein the pair of the second electrodes are arranged to be substantially perpendicular to a direction extending from the second air inlet of the second sensing device toward the second air outlet of the second sensing device.

7. The detection apparatus of claim 1, wherein the first sensing device is free of a sensing material capable of electrochemically reacting with the gas flowing into the first sensing device.

8. The detection apparatus of claim 1, wherein the second sensing device is free of a sensing material capable of electrochemically reacting with the first filter with the solid.

9. The detection apparatus of claim 3, further comprising a pump connected to the first gas inlet of the first sensing device.

10. A detection apparatus for detecting a gas generated from semiconductor manufacturing, comprising:
   a first device configured to apply a first alternating current signal to obtain a first response associated with the gas flowing through the first device, wherein the first device is free of a sensing material capable of electrochemically reacting with the gas flowing through the first device;
   a second device configured to apply a second alternating current signal to obtain a second response associated with a solid in the gas flowing through the second device, wherein the second device is free of a sensing material capable of electrochemically reacting with the solid in the gas flowing through the second device; and
   an analyzer configured to receive the first response and the second response and generate at least one impedance spectrum based on the first response and the second response;
   wherein the gas comprises an acid gas and an alkaline gas, and wherein the solid comprises a salt solid.

11. The detection apparatus of claim 10, wherein the first device is configured to obtain the first response associated with the gas passing through a first filter disposed within the first device.

12. The detection apparatus of claim 10, wherein the second device comprises a second filter configured to collect the solid in the gas, and wherein the second device is configured to obtain the second response associated with the solid collected by the second filter.

13. The detection apparatus of claim 12, wherein the second device is configured to obtain a third response regarding the gas flowing through the second filter, and wherein the analyzer is configured to receive the third response and result the at least one impedance spectrum based on the first response, the second response and the third response.

14. The detection apparatus of claim 10, wherein the first device is configured to obtain the first response associated with the gas passing through a through hole within the first device.

15. The detection apparatus of claim 10, further comprising a pump configured to introduce the gas into the first device.

16. The detection apparatus of claim 15, wherein the first device is in fluid communication with the second device, and wherein the gas flows through the first device and then flows through the second device.

17. A method of detecting a characteristic of a gas generated from semiconductor manufacturing, comprising:

providing the gas flowing into a first device;

applying a first alternating current signal directly to the gas in the first device so as to obtain a first response;

providing the gas flowing from the first device into a second device;

applying a second alternating current signal directly to a first filter disposed in the second device and configured to collect a solid in the gas in the second device so as to obtain a second response; and generating at least one impedance spectrum based on the first response and the second response;

wherein the gas comprises an acid gas and an alkaline gas, and wherein the solid comprises a salt solid.

18. The method of claim 17, further comprising:

identifying a characteristic of the gas based on the at least one impedance spectrum.

19. The method of claim 17, wherein the first device is free of a sensing material capable of electrochemically reacting with the gas when applying the first alternating current signal.

20. The method of claim 17, wherein the second device is free of a sensing material capable of electrochemically reacting with the first filter when applying the second alternating current signal.

* * * * *